United States Patent
Rocco

(10) Patent No.: US 9,462,680 B2
(45) Date of Patent: Oct. 4, 2016

(54) PRINTED CIRCUIT BOARD

(71) Applicant: Robert Bosch (Australia) Pty. Ltd, Clayton (AU)

(72) Inventor: Tony Rocco, Elwood (AU)

(73) Assignee: ROBERT BOSCH (AUSTRALIA) PTY. LTD, Clayton (AU)

( * ) Notice: Subject to any disclaimer, the term of this patent is extended or adjusted under 35 U.S.C. 154(b) by 89 days.

(21) Appl. No.: 13/779,474

(22) Filed: Feb. 27, 2013

(65) Prior Publication Data

US 2013/0222796 A1 Aug. 29, 2013

(30) Foreign Application Priority Data

Feb. 29, 2012 (AU) .............................. 2012 900 790

(51) Int. Cl.
  *H05K 7/00* (2006.01)
  *H05K 1/02* (2006.01)
  *G01N 21/956* (2006.01)
  *H05K 3/34* (2006.01)

(52) U.S. Cl.
  CPC .......... *H05K 1/0269* (2013.01); *G01N 21/956* (2013.01); *G01N 2021/95646* (2013.01); *G01N 2021/95653* (2013.01); *H05K 1/0203* (2013.01); *H05K 3/3421* (2013.01); *H05K 2201/09072* (2013.01)

(58) Field of Classification Search
  USPC ........................................ 361/760, 761, 748
  See application file for complete search history.

(56) References Cited

U.S. PATENT DOCUMENTS

| 5,062,567 A | 11/1991 | Crossley |
| 5,612,576 A * | 3/1997 | Wilson et al. ................. 257/788 |
| 6,490,166 B1 | 12/2002 | Ramalingam et al. |
| 8,273,607 B2 * | 9/2012 | Park et al. ..................... 438/127 |
| 2002/0131240 A1 | 9/2002 | Kim |
| 2008/0023214 A1 | 1/2008 | Kuo |
| 2008/0115967 A1 | 5/2008 | Giboney et al. |

FOREIGN PATENT DOCUMENTS

| JP | 1258454 | 10/1989 |
| JP | 10189863 | 7/1998 |
| JP | 2010040781 | 2/2010 |

* cited by examiner

*Primary Examiner* — Andargie M Aychillhum
(74) *Attorney, Agent, or Firm* — Norton Rose Fulbright US LLP

(57) ABSTRACT

A printed circuit board including a substrate of electrically insulating material and a pattern of electrically conducting paths formed on at least one side of the substrate. One or more electronic components mounted to the substrate in connection with the electrically conductive paths. At least one of the components including a base solder connection between a base surface and a facing conducting surface of the component. The base solder connection is substantially obscured from view from the side of the substrate to which the component is attached and an opening is provided extending through the substrate beneath the base surface of the component so that the base solder connection is visible through the opening.

18 Claims, 2 Drawing Sheets

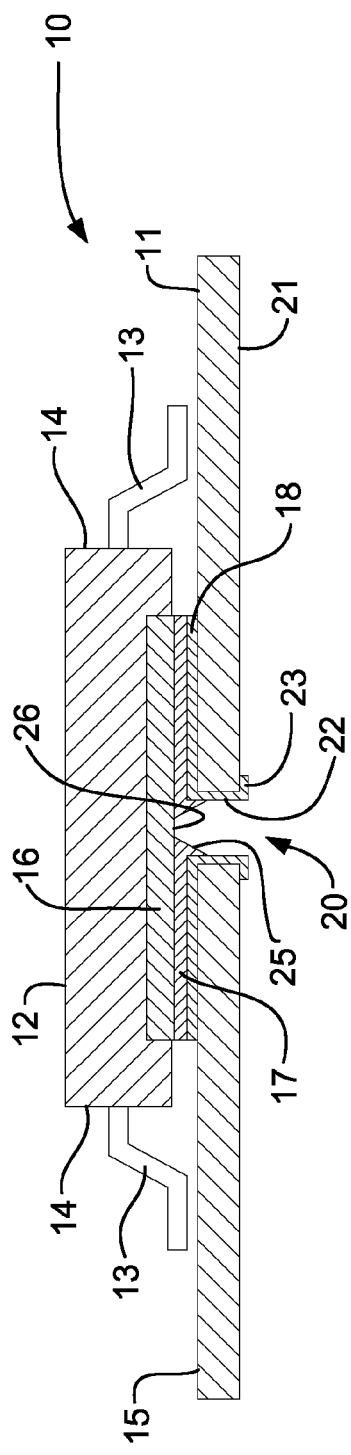
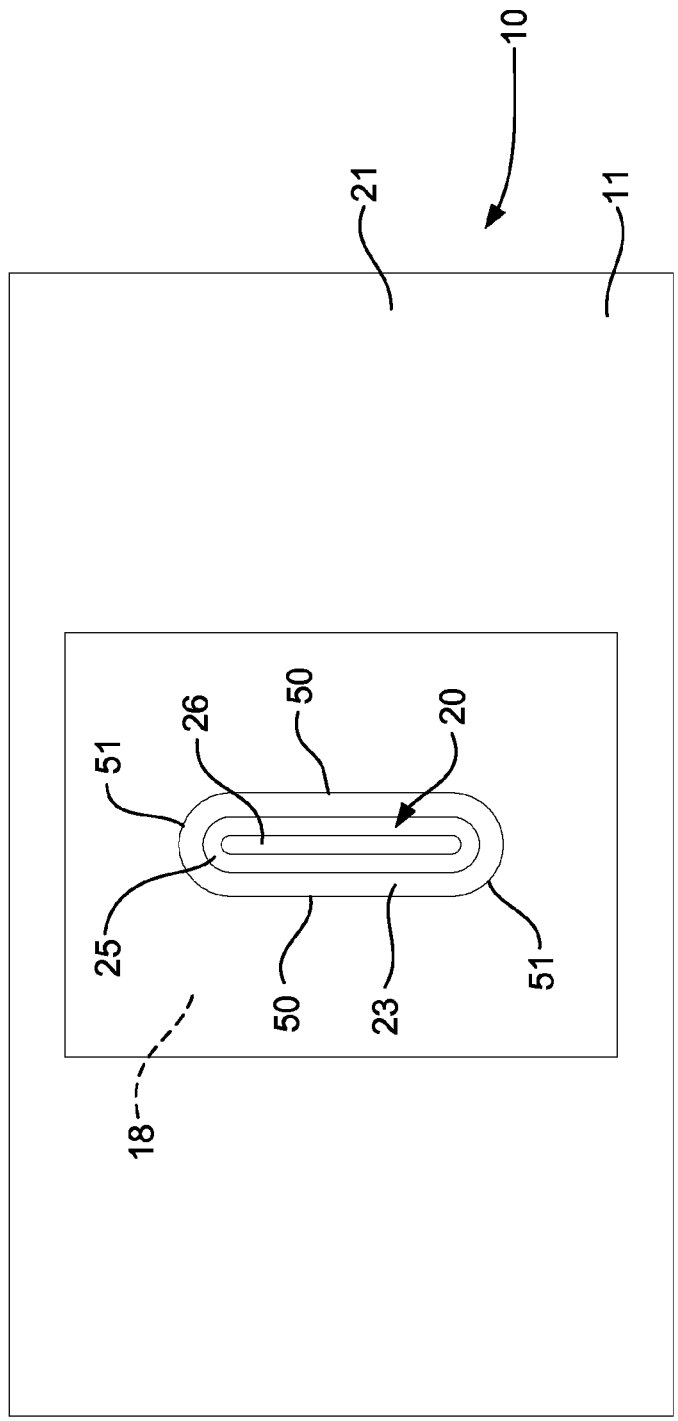

PRINTED CIRCUIT BOARD

RELATED APPLICATION INFORMATION

The present application claims priority to and the benefit of Australian Patent Application No. 2012 900 790, which was filed in Australia on Feb. 29, 2012, the disclosure of which is incorporated herein by reference.

FIELD OF THE INVENTION

A printed circuit board (PCB) is a substrate that forms part of a surface mount assembly (SMA) which is used in electronic devices and equipment to connect components electronically. The present invention relates to the construction of PCBs and SMAs, in particular relating to the secure attachment of components to the PCB to form an SMA.

BACKGROUND INFORMATION

It is to be noted that the expression PCB can be used in industry to describe just the substrate of an SMA, particularly a substrate which has been etched or plated with a solder mask, but which has not yet had electronic components fixed thereto by soldering, or it can be used to describe a finished SMA which has electronic components fixed to the substrate. Reference herein to a PCB is intended to cover both of these uses of the expression PCB, although where appropriate, reference will also be made to the expression SMA, which will describe a completed assembly which includes a PCB as the substrate to which electronic components are fixed.

A PCB normally comprises a copper sheet which is bonded to one or both sides of a non-conductive substrate. The non-conductive substrate can be a resin for example or a nonporous polytetrafluoroethylene (PTFE). Parts of the copper sheet can then be removed, such as by etching, to create electrical paths on the surface of the substrate to connect electronic components. Alternatively, the copper paths can be added to the surface of the substrate by plating, but this is a less popular approach.

The electrical paths lead to points for component connection, so that two or more components can be connected electrically by connection to the board. The normal connection of the components to the copper paths of the PCB is by solder. Where copper sheet is bonded to both sides of a non-conductive substrate, electrical connection can be made between the copper sheets on either side of the substrate by holes drilled through the substrate (known as "vias") which are plated with a conductive metal, i.e. copper. Thus, there is an electrical bridging between the copper sheets so that components can be connected to either side of the PCB and still be in electrical connection.

Some PCBs include more than two layers of copper with one or more layers embedded in the substrate. In these PCBs adjacent layers can be connected by vias that do not necessarily extend fully through the substrate.

Exposed copper paths can be covered with a suitable coating to prevent damage to the paths by corrosion. The coating can be a solder mask, or a nickel or gold layer for example. The points for component connection can also be covered for corrosion protection, although the coverage can be different so as not to prevent connection of a component to the PCB by solder. In some PCBs, the connection points are plated with tin which prevents the points from corroding prior to component connection, but which melts away easily during the soldering process to expose the connection surface.

SMAs including a PCB substrate can be manufactured almost entirely automatically. As a result, SMAs are relatively inexpensive and suitable for high volume manufacture. To ensure reliability of operation of an SMA, part of the manufacturing process involves inspection of each solder connection between an electronic component and the PCB substrate. Advantageously, the inspection process can be by automatic optical inspection (AOI).

AOI is very suitable for inspecting solder connections which are visible on the surface of the PCB once the connection has been made. The AOI process is also suitable for inspecting connections on both sides of a PCB as the PCB can be easily turned from one side to the other. However, some electronic components are connected to the PCB via connections that are not visible once they are made. For example, the base of a component known as a "semiconductor package" or an "integrated circuit" can include a component known in the industry as an "exposed pad" or otherwise known as a "heat slug" (hereinafter an "exposed pad") which connects to the PCB substrate by a solder connection that is not visible once the connection is made. Exposed pads can be provided for example to conduct heat away from the semiconductor package or integrated circuit and to improve the electrical connection of the package or circuit to the PCB substrate. Thus, exposed pads can increase the removal of waste heat and the delivery of electric current to the package or circuit so that the capacity of the component and thus the SMA can be increased.

An exposed pad is normally connected to the PCB substrate by a solder connection. That solder connection once made, is hidden or concealed between the semiconductor package or integrated circuit and the PCB substrate. Connections of this kind are generally made in addition to the normal visible connections made for these components and known to persons skilled in the art.

Hidden joints of the kind discussed above still require inspection to ensure a proper and secure connection has been made between the component and the conducting surface of the substrate. To date, X-ray inspection for hidden or concealed connections has been made. However this is costly in terms of the initial investment in the X-ray equipment, and inspection by X-ray introduces an extra step in the inspection process and thus increases the cycle time for SMA manufacture.

SUMMARY OF THE INVENTION

The exemplary embodiments and/or exemplary methods of the present invention have thus been developed with a view to reduce or even eliminate the need for X-ray inspection of hidden connections in SMAs.

According to the exemplary embodiments and/or exemplary methods of the present invention there is provided a printed circuit board including a substrate of electrically insulating material and a pattern of electrically conductive paths formed on at least one side of the substrate, a plurality of electronic components mounted to the substrate in connection with the electrically conductive paths, at least one electronic component including a base solder connection between a base surface of the component and a facing conducting surface of the substrate, the base solder connection being substantially obscured from view from the side of the substrate to which the component is attached, an opening extending through the substrate beneath the base surface of the component so that the base solder connection is visible through the opening for inspection.

A PCB according to the exemplary embodiments and/or exemplary methods of the present invention advantageously allows inspection by AOI of an otherwise hidden or concealed connection, by virtue of the opening which is provided through the substrate beneath the base surface of the electronic component. The solder connection between the base surface of the component and the facing conducting surface of the substrate can be inspected through the opening by AOI without the need for X-ray inspection. Thus, and advantageously, the installation of X-ray machinery is not required for inspection purposes and the extra inspection step required by X-ray can be eliminated in the PCB manufacturing process. Moreover, the inspection of the base solder connection through the opening by AOI does not prolong the manufacturing process, as AOI is already used to inspect other visible solder joints made to the PCB. The exemplary embodiments and/or exemplary methods of the present invention thus add another connection to be inspected by AOI, but this adds negligibly to the manufacturing cycle time.

The opening which extends through the substrate may extend through the conducting surface of the substrate to which the base surface of the component is soldered. This arrangement will only usually be clearly evident in the PCB prior to the attachment of the electronic component to the conducting surface and in that state, the opening will open into or through the conducting surface, i.e. the conducting surface will extend to the edge of the opening at the surface of the substrate, or adjacent to the edge of the opening, or even into the opening. In addition, the opening, or the wall of the opening, may be plated partially or fully with a conductive material such as a metal, and the preference is for the plating of the opening to be contiguous or substantially contiguous with the conducting surface of the substrate. Thus, the plating of the opening can connect with or to the conducting surface of the substrate and the connection can be within the opening, at the edge of the opening or at the surface of the substrate. The plating can, for example extend out of the opening for connection with the conducting surface.

The conductive material of the opening, can be of any suitable material and can be the same as that which forms the electrically conductive paths of the PCB, or as applied to other openings or vias of the PCB which connect between conductive layers of the PCB. The plating for example can be a metal plating such as copper.

The arrangements described above are intended to facilitate the solder of the base solder connection to extend from the conducting surface of the substrate into the opening of the substrate in connection with the conductive plating of the opening for the following reasons.

The advantage of plating the opening with a conductive material such as a metal, and ensuring the solder of the base solder connection extends into the opening in connection with the plating applied to the opening, is that the solder can form a solder fillet within the opening and that fillet can be readily inspected by AOI. The inspection of the fillet can thus determine whether the solder connection has been properly made and passes the inspection criteria. The AOI process will look for characteristics of the solder connection to determine whether it passes or fails the inspection process and those characteristics will be evident in a solder fillet that forms on the plated surface of the opening. While the invention extends to the inspection of solder connections made between a component and the conducting surface of the substrate and which do not include a portion that extends into or which connects with the surface of the opening, the preference is for the solder connection to extend into the opening and to form a fillet, as that presents the solder in a convenient form for AOI.

It is to be understood that the reference to the formation of a solder fillet on the plated surface of the opening is not to be understood as requiring a particular shape of fillet. This reference requires a portion of the solder connection between the component and the conducting surface of the substrate to enter the opening in connection with the plated surface of the opening. The entry of solder forms the fillet and the form of fillet can be of any suitable form or shape. The amount of entry can be of any suitable amount to produce the required connection and to facilitate AOI. The amount of entry can be from very small to larger. In fact, the invention contemplates the fillet being formed so as not to enter the opening but rather, just to exist above the opening and in that form of the invention, the opening need not be plated. However, the preference is to plate the opening as discussed above and to have the fillet enter the opening in contact with the plating.

In some forms of the invention, the solder fillet will be formed continuously and will be continuous along the plated wall of the opening at the end of the opening which is proximate the base surface of the component. Thus, the solder connection can be formed in a continuous ring about the opening. Alternatively, in other forms of the invention, the solder fillet is formed discontinuously so as to be discontinuous along the wall of the opening at the end of the opening that is proximate the base surface of the component. Forming the fillet discontinuously along the wall of the opening can provide advantages in some forms of the invention, by improving the detection of voids in the solder connection which affect the connection between the component and the PCB. Thus, by improving the detection of solder voids, the inspection process improves the likelihood of detecting solder connections which should fail the inspection process.

The improvement in the detection of solder voids by forming the solder fillet discontinuously occurs because by separating the solder into sections, voids that are formed in one section of the fillet are prevented from jumping or travelling into other sections. Thus, they are quarantined. This means they are more easily detected by AOI as a concentrated body of voids as compared to if the voids spread throughout the fillet.

In the forms of the invention in which the solder fillet is formed discontinuously, such as along the wall of the opening, the fillet can include one gap or break, or it can be formed in any number of separated fillet sections, such as one two sections (with two gaps or breaks), three sections (with three gaps or breaks), four sections or more. Moreover, the sections can be of equal dimension, or unequal dimension. It has been envisaged to date, that in a one aspect of the exemplary embodiments and/or exemplary methods of the present invention, the solder fillet could be formed in four separated fillet sections of equal length.

In order to create the separated fillet sections, in some forms of the invention, the conducting surface of the substrate to which the base surface of the electronic component is soldered, is interrupted at or adjacent the opening. In other words, the conducting surface of the substrate is interrupted by a break or gap at or adjacent the opening so that the solder fillet will not bridge the interruption and so itself will include a corresponding break or gap, and so will form one or more individual fillet sections which are not connected to adjacent fillet sections. In some forms of the invention, the opening of the substrate forms a void in the conducting surface and one or more breaks or gaps in the conducting surface extend from the opening through the conducting surface away from the opening. These breaks or gaps can extend linearly. In some forms of the invention, the breaks or gaps extend to the edge of the conducting surface remote from the opening. In other forms of the invention, the breaks or gaps extend away from the opening but terminate prior to the edge of the conducting surface remote from the opening. The breaks or gaps can thus extend for only a short distance away from the opening or for a longer distance. The breaks or gaps can also be formed in the plating of the opening if provided and they can align with the breaks or gaps of the conducting surface.

Any number of breaks or gaps in the conducting surface of the substrate can be provided as indicated above to create the required number of breaks or gaps in the solder fillet. Regardless of the manner with which those breaks or gaps are made in the conducting surface of the substrate, the intention is that upon soldering the component to the conducting surface, the fillet which is formed on the wall of the opening is discontinuous at the or each break or gap.

In some forms of the invention, the conducting surface is formed as a square or rectangular surface. In other forms of the invention, the conducting surface can be otherwise shaped such as circular or oval.

The opening formed in the substrate can be formed substantially centrally of the conducting surface or can be offset from central.

The opening which is formed through the substrate can be of any suitable shape and configuration. Accordingly, the opening can be substantially round or substantially oval, or the opening could be elongate, having straight sides and curved ends for example (obround). Typically the opening would be drilled or routed by normal PCB manufacturing equipment. The opening for example, could be formed in the same way as a via is formed and plated in the same manner. Thus, the opening requires no sophisticated manufacturing process beyond processes already employed for the manufactures of PCBs.

The solder connection made between the base surface of the component and a facing conducting surface of the substrate is not intended to replace solder connections already made between components and the substrate, usually between legs of the components and the substrate. Those connections can continue to be made in addition to the base solder connection described above and can continue to be inspected by AOI. The addition of the solder connection made between the base surface of the component and a facing conducting surface of the substrate can be made for the advantageous reasons discussed above in relation to the use of exposed pads.

The base surface of the electronic component can include an exposed pad of the kind discussed above so that the connection between the component and the conducting surface is between the exposed pad and the conducting surface. The exposed pad can be an integral part of the component.

The exemplary embodiments and/or exemplary methods of the present invention also extend to a substrate for a printed circuit board which is formed according to the previous discussion for the connection of an electronic component to a conducting surface of the substrate. Thus, the substrate will include a conducting surface to which an electronic component is to be connected by solder, and an opening will extend through the substrate within the conducting surface, in some cases substantially centrally of that surface. The opening can extend through the conducting surface. A substrate according to the invention can include a plurality of conducting surfaces and a plurality of openings extending through those surfaces for the purpose of AOI of solder connections made between an electronic component and the conducting surface. The openings can be plated to enable a solder fillet to form on the surface of the opening.

All aspects of the PCB discussed above as they relate to the construction of the substrate component of the PCB but without electronic components mounted thereon are within the scope of the exemplary embodiments and/or exemplary methods of the exemplary embodiments and/or exemplary methods of the present invention.

The exemplary embodiments and/or exemplary methods of the present invention also provide a method of inspecting a PCB of the kind described above, whereby the method includes orienting the PCB so that an AOI device can view into an opening formed through the substrate of the PCB to inspect a solder made between the base surface of an electronic component and a facing conducting surface of the substrate, and the method including inspecting the solder connection.

In order that the exemplary embodiments and/or exemplary methods of the present invention may be more fully understood, some embodiments will now be described with reference to the figures.

BRIEF DESCRIPTION OF THE DRAWINGS

FIG. 1 is a cross sectional view taken through an integrated circuit (IC) package as shown soldered to the substrate of a portion of a PCB in accordance with the invention.

FIG. 2 is a plan view from underneath of a portion of the PCB illustrated in FIG. 1.

DETAILED DESCRIPTION

Figure 3:
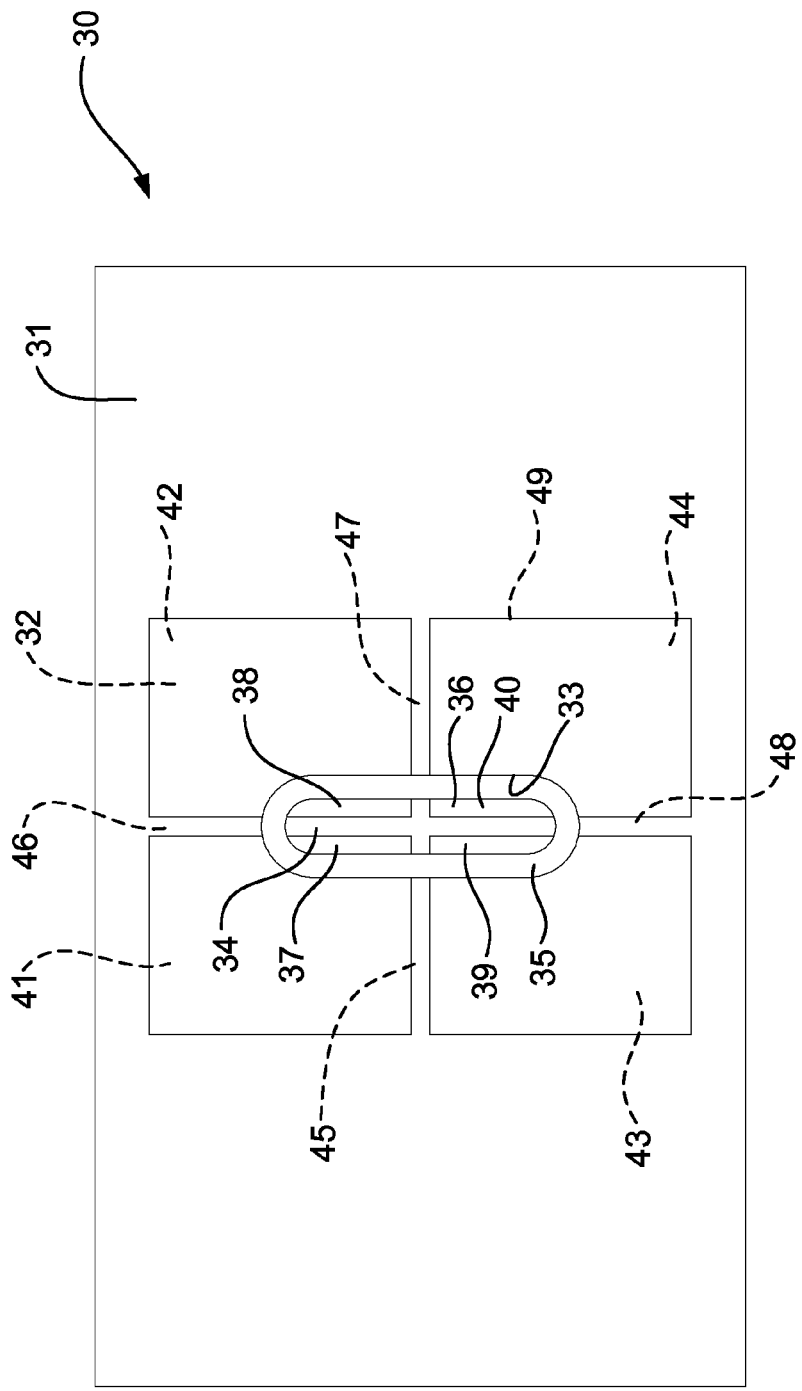
FIG. 3 is a plan view from underneath of a portion of a PCB of an alternative arrangement in accordance with the invention.

Referring to FIGS. 1 and 2, a portion of a PCB 10 is illustrated in cross sectional view and underneath view respectively which includes a substrate 11, an integrated circuit or IC package 12 and legs 13 that extend from opposite side edges 14 of the package 12 into contact with an upper surface 15 of the substrate 11. While the legs 13 are shown slightly spaced from the upper surface 15 in FIG. 1, it is normal practice to fix the package 12 to the substrate 11, by soldering the legs 13 to a conductive portion of the surface 15 and by that connection, facilitating passage of electric current from conductive portion of the surface 15, through the legs to the IC package.

The IC package 12 includes an "exposed pad" or "heat slug" 16 which is formed as an integral part of the bottom surface of the package 12 and which is positioned to face the upper surface 15 of the substrate 11. A solder connection 17 connects the exposed pad 16 and thus the IC package 12 to a conducting surface 18 of the substrate 11. The conducting surface 18 is shown in outline in FIG. 2 as it would not normally be apparent from the underneath view of FIG. 2. The solder connection 17 is substantially hidden or concealed between the exposed pad 16 and the conducting surface 18 when viewed from above the PCB 10. However, the solder connection 17 must be inspected for evidence of failure to ensure proper connection between the exposed pad 16 and the conducting surface 18 and as explained above, in prior art arrangements, X-ray inspection is normally adopted for that purpose.

In accordance with the invention, FIG. 1 illustrates an opening 20 which extends through the substrate 11, from the upper surface 15 to the lower surface 21.

The opening 20 includes a conductive plating 22 formed on the wall of the opening 20. It can be seen from FIG. 1 that the plating 22 forms a lip 23 at the lower surface 21 and extends upwardly along the wall of the opening 20 to the upper surface 15. At the upper surface 15, the plating 22 joins the conducting surface 18 so that the conducting surface 18 is contiguous with the plating 22. The plating 22 extends fully about the opening 20 as is evident in FIG. 2, which shows the lip 23 of the plating 20 formed continuously on the underneath side of the substrate 11. As indicated above, the plating 22 can be of any suitable material to which a solder can adhere, and that includes types of metals such as copper.

It can be seen from FIGS. 1 and 2, that the solder connection 17 extends fully along the length of the exposed pad 16 and the conducting surface 18. Moreover, it is evident that the solder connection 17 includes a fillet 25 that extends into the opening 20, in connection with the plating 22 at the end of the opening 20 which is proximate the exposed pad 16. As shown in FIG. 2, the fillet 25 is continuous about the opening 20.

It should be noted that extension of the fillet 25 into the opening 20 is not essential to form a fillet. A fillet could be formed without extending into the opening 20, but the preference is for the fillet to extend into the opening 20.

With reference to FIG. 2, the fillet 25 is visible from the underneath of the substrate 11, while a central portion 26 of the opening 20 includes a thin layer of solder which is pulled into the central portion 26 by surface tension during the soldering process. AOI of the fillet 25 can determine whether the solder connection 17 between the exposed pad 16 and the conducting surface 18 is properly made and should pass the inspection process.

It will also be evident from FIG. 2, that only a very small portion of the surface area of the exposed pad 16 is not in soldered connection with the conducting surface 18. Only the portion 26 of the exposed pad 16 is not in soldered connection with the conducting surface 18, given that the solder fillet 25 forms a connection with the exposed pad about the portion 26. Thus, provision of an opening 20 does not compromise the connection of the IC package 12 to the substrate 11.

FIG. 3 is similar to FIG. 2, the difference being that the conducting surface 18 of FIG. 2 is interrupted by breaks or gaps to form the conducting surface 32 and to create a discontinuous fillet. In FIG. 3, a portion of a PCB 30 is illustrated from underneath (the same view as FIG. 2) which includes a substrate 31 and the outline of a conducting surface 32. The conducting surface is applied to the upper surface of the substrate 31 and therefore would not ordinarily be visible in FIG. 3, but is only shown in FIG. 3 for the purposes of explanation. An opening 33 is formed through the substrate 31 and through the conducting surface 32 and through that opening a central portion 34 can be seen, which has a thin solder layer applied thereto in the same manner as the central portion 26 of the PCB 10. The opening 33 is plated with a conductive metal and a lip 35 of the plating extends a small distance across the underneath surface of the substrate 31 as illustrated in FIG. 3. In this respect, the arrangement of FIG. 3 is the same as the PCB 10 of FIGS. 1 and 2.

A solder fillet 36 is illustrated in FIG. 3 and is formed discontinuously about the opening 33 by four solder fillet sections 37 to 40. This fillet construction is advantageous as described earlier herein because it permits improved detection of solder voids by separating the solder into sections, because voids that are formed in one section of the fillet are prevented from jumping or travelling into other sections. The voids are thus more easily detected by AOI as compared to if they are spread throughout the fillet 36.

To form the fillet sections 37 to 40, the conducting surface 32 can be formed into four separated sections 41 to 44, to form breaks or gaps 45 to 48 (hereinafter gaps), which extend from the outer edge 49 of the conducting surface 32 inwardly and through to the upper end of the opening 33. By forming the conducting surface 32 into four separated sections 41 to 44 by the gaps 45 to 48, the solder connection between the exposed pad and the conducting surface 32 is confined to the conducting sections 41 to 44 of the surface 32 because the gaps 45 to 48 do not facilitate solder connection. Likewise, the fillet 36 cannot form continuously about the opening 33 because the fillet 36 cannot jump the gaps 45 to 48, but rather is formed only in the sections of the opening 33 where the conducting surface 32 exists, i.e. in the sections 41 to 44. Thus, a discontinuous fillet 36 is formed.

It is to be noted that the gaps 45 to 48 do not need to extend completely to the edge 49 of the conductive surface 32 as shown in FIG. 3, but rather can terminate inboard of that edge and still form a discontinuous fillet. Also, the example of four gaps 45 to 48 is one example only and the number of gaps could be greater or lesser.

The openings 20 and 33 as shown in the figures are formed to have a pair of straight sides 50 and a pair of curved ends 51 (see FIG. 2). This shape is known as an "obround" shape. Of course, the openings could take other shapes, such as round or oval. The openings 20 and 33 are formed by routing, but they could equally be formed by other machining methods such as drilling.

The invention described herein is susceptible to variations, modifications and/or additions other than those specifically described and it is to be understood that the invention includes all such variations, modifications and/or additions which fall within the spirit and scope of the present disclosure.

Throughout the description and claims of this specification the word "comprise" and variations of that word, such as "comprises" and "comprising", are not intended to exclude other additives, components, integers or steps.

What is claimed is:

1. A printed circuit board, comprising:
   a substrate of electrically insulating material and a pattern of electrically conductive paths formed on at least one side of the substrate;
   a plurality of electronic components mounted to the substrate in connection with the electrically conductive paths; and
   at least one electronic component including a base solder connection between a base surface of the component and a facing conducting surface of the substrate;
   wherein the base solder connection is substantially obscured from view from the side of the substrate to which the electronic component is attached, and wherein an inspection opening, which is plated with metal, extends through the substrate beneath the base surface of the electronic component and the base solder connection extends into the opening in connection with the metal plating, so that the base solder connection is visible through the opening for inspection of the base solder connection.

2. The printed circuit board of claim 1, wherein the opening is plated with copper.

3. The printed circuit board of claim 2, wherein the conducting surface of the substrate and the plating of the opening is substantially contiguous.

4. The printed circuit board of claim 1, wherein the solder that extends into the opening forms a solder fillet within the opening.

5. The printed circuit board of claim 4, wherein the opening defining a wall extending between opposite sides of the substrate and the solder fillet is continuous along the wall of the opening at the end of the opening that is proximate the base surface of the component.

6. The printed circuit board of claim 4, wherein the opening defining a wall extending between opposite sides of the substrate and the solder fillet is discontinuous along the wall of the opening at the end of the opening that is proximate the base surface of the component.

7. The printed circuit board of claim 6, wherein the solder fillet is formed in at least two separated fillet sections.

8. The printed circuit board of claim 6, wherein the solder fillet is formed in four separated fillet sections.

9. The printed circuit board of claim 6, wherein the conducting surface of the substrate to which the base surface of the electronic component is soldered is interrupted adjacent the opening so that the solder fillet does not form on the wall of the opening at the interruption.

10. The printed circuit board of claim 9, wherein the conducting surface of the substrate is interrupted adjacent the opening in at least two positions so that the solder fillet is formed in at least two separated fillet sections.

11. The printed circuit board of claim 9, wherein the conducting surface of the substrate is interrupted adjacent the opening at four positions so that the solder fillet is formed in four separated fillet sections.

12. The printed circuit board of claim 1, wherein the opening is substantially round.

13. The printed circuit board of claim 1, wherein the opening is substantially oval.

14. The printed circuit board of claim 1, wherein the opening is elongate and having straight sides and curved ends.

15. A substrate for a printed circuit board arrangement, comprising:
a substrate of electrically insulating material and a pattern of electrically conductive paths formed on at least one side of the substrate;
wherein the printed circuit board arrangement includes:
a plurality of electronic components for mounting to the substrate in connection with the electrically conductive paths; and
at least one electronic component including a base solder connection between a base surface of the component and a facing conducting surface of the substrate;
wherein the base solder connection is substantially obscured from view from the side of the substrate to which the electronic component is to be attached, and wherein an inspection opening, which is plated with metal, extends through the substrate beneath the base surface of the component and the base solder connection extends into the opening in connection with the metal plating, so that the base solder connection is visible through the opening for inspection of the base solder connection.

16. A method of inspecting a printed circuit board, the method comprising:
orienting the printed circuit board so that an automatic optical inspection device can view into an inspection opening, which is plated with metal, through the substrate of the printed circuit board to inspect a solder connection made between the base surface of an electronic component and a facing conducting surface of the substrate, and inspecting the solder connection;
wherein the printed circuit board includes:
the substrate, the substrate being of electrically insulating material and having a pattern of electrically conductive paths formed on at least one side of the substrate;
a plurality of electronic components mounted to the substrate in connection with the electrically conductive paths; and
the electronic component including a base solder connection between the base surface of the component and the facing conducting surface of the substrate;
wherein the base solder connection is substantially obscured from view from the side of the substrate to which the electronic component is attached, and wherein the inspection opening extends through the substrate beneath the base surface of the component and the base solder connection extends into the opening in connection with the metal plating, so that the base solder connection is visible through the opening for inspection of the base solder connection.

17. The method of claim 16, wherein the solder extends into the opening and forms a solder fillet within the opening and the automatic optical inspection device is operable to inspect the solder fillet.

18. A printed circuit board, comprising:
a substrate of electrically insulating material and a pattern of electrically conductive paths formed on at least one side of the substrate;
a plurality of electronic components mounted to the substrate in connection with the electrically conductive paths;
at least one electronic component including a base solder connection between a base surface of the component and a facing conducting surface of the substrate, wherein the base solder connection is substantially obscured from view from the side of the substrate to which the electronic component is attached; and
an inspection means for inspecting the base solder connection, wherein the inspection means includes an inspection opening plated with metal and extending through the substrate beneath the base surface of the electronic component and the base solder connection extends into the opening in connection with the metal plating, so that the base solder connection is visible for inspection through the opening.

* * * * *